(12) United States Patent
Spinks et al.

(10) Patent No.: US 6,770,059 B1
(45) Date of Patent: Aug. 3, 2004

(54) CURVED TIP FOR AN INSERTION DEVICE

(75) Inventors: Thomas L. Spinks, Sylvania, OH (US); Kevin H. Pike, Ypsilanti, MI (US)

(73) Assignee: Span-America Medical Systems, Inc., Greenville, SC (US)

(*) Notice: Subject to any disclaimer, the term of this patent is extended or adjusted under 35 U.S.C. 154(b) by 116 days.

(21) Appl. No.: 09/698,621

(22) Filed: Oct. 27, 2000

Related U.S. Application Data

(60) Provisional application No. 60/162,322, filed on Oct. 28, 1999.

(51) Int. Cl.[7] .................. A61M 25/00; A61M 5/178
(52) U.S. Cl. ................... 604/264; 604/164.01
(58) Field of Search ................. 604/264–275, 604/164.01

(56) References Cited

U.S. PATENT DOCUMENTS

| | | | |
|---|---|---|---|
| 3,421,509 A | * | 1/1969 | Fiore ............ 604/271 |
| 4,588,398 A | * | 5/1986 | Daugherty et al. ......... 604/265 |
| 4,661,300 A | | 4/1987 | Daugherty |
| 4,790,830 A | | 12/1988 | Hamacher |
| 5,011,478 A | | 4/1991 | Cope |
| 5,053,020 A | | 10/1991 | Manchester |
| 5,205,830 A | | 4/1993 | Dassa et al. |
| 5,234,416 A | | 8/1993 | Macaulay et al. |
| 5,417,665 A | | 5/1995 | De La Mata et al. |
| 5,425,903 A | | 6/1995 | Sloane, Jr. et al. |
| 5,472,417 A | | 12/1995 | Martin et al. |
| 5,472,435 A | | 12/1995 | Sutton |
| 5,505,713 A | | 4/1996 | Van Antwerp |
| 5,514,112 A | * | 5/1996 | Chu et al. ............. 604/267 |
| 5,683,370 A | | 11/1997 | Luther et al. |

FOREIGN PATENT DOCUMENTS

WO    WO 98/4880 A1    11/1998

OTHER PUBLICATIONS

Copy of International Search Report established for International Patent Application No. PCT/US98/08385.

* cited by examiner

*Primary Examiner*—Edward K. Look
*Assistant Examiner*—Michael Leslie
(74) *Attorney, Agent, or Firm*—Gardner Carton & Douglas LLP

(57) ABSTRACT

The present invention is directed to an insertion device, such as a catheter, including a tip having a hollow, substantially radial cross sectional configuration and a substantially parabolic longitudinal configuration with a circular tip curvature. The outer wall of the novel tip of the invention is completely curved, and contains no straight or angled outer walls within the length of the tip. The inner wall of the tip defines a substantially straight passageway through which a piercing device such as a needle may be inserted.

11 Claims, 2 Drawing Sheets

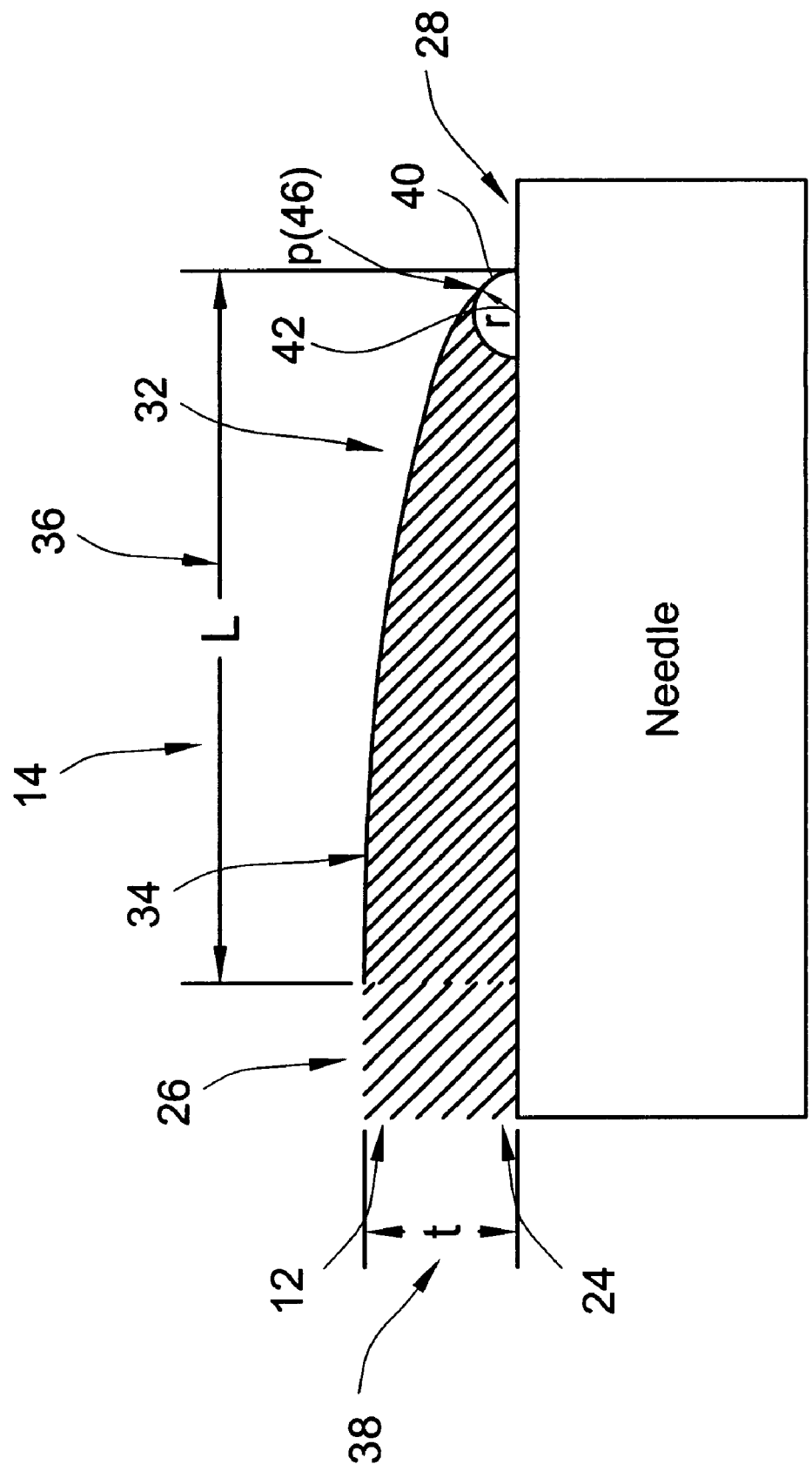

CURVED TIP FOR AN INSERTION DEVICE

This application claims the benefit of U.S. Provisional Application No. 60/162,322, filed Oct. 28, 1999.

FIELD OF THE INVENTION

The present invention relates to a tip for an insertion device. More specifically, the invention is directed to a curved tip for an insertion device such as a catheter. The surface profile of the novel tip of the invention is completely curved and includes a generally parabolic tubular surface profile with an insertion end that assumes a generally circular surface profile.

BACKGROUND OF THE INVENTION

A catheter is usually inserted through the skin of a patient by use of a sharp instrument, such as a needle. In many applications, the needle extends through the catheter wherein the point of the needle is adjacent to and extending slightly beyond the tip of the catheter. The needle pierces the skin of the patient to form an opening and the tip of the catheter follows the needle into the opening.

Traditional catheter tips generally have straight edges and blunt insertion ends. The bluntness of traditional tips impedes the forward progress of the catheter into the opening in the skin. The force required to insert a blunt ended, straight edged catheter tip into the skin, which is also known as "transition force," is generally sufficiently high to cause pain to the patient upon insertion.

Attempts have been made to reduce the transition force required to insert a catheter into the skin of a patient. An example of such a catheter is shown in U.S. Pat. No. 4,588,398. In this patent, the tip of the catheter is angular, although still with straight edges and a blunt insertion end.

It has been found that there is a need for a catheter tip that provides for the smooth and easy transition from a needle to a catheter as the device moves through the skin, to reduce the transition force during insertion of a catheter into a patient. The present invention satisfies this need.

SUMMARY OF THE INVENTION

The present invention is directed to an insertion device, such as a catheter, including a tip having a hollow, substantially radial cross sectional configuration and a substantially parabolic longitudinal configuration with a longitudinally circular tip curvature. The outer wall of the novel tip of the invention is completely curved, and contains no straight or angled outer walls within the length of the tip. The inner wall of the tip defines a substantially straight passageway through which a piercing device such as a needle may be inserted.

An embodiment of the present invention provides an insertion device that reduces the transition force required to insert the device into the skin of a patient.

An embodiment of the present invention also provides a tip for an insertion device having an entirely curved outer wall in the longitudinal dimension.

An embodiment of the invention further provides a catheter tip configuration which is thin enough to reduce the above-referenced transition force yet tough enough to eliminate splitting, tearing, or bunching of the catheter tubing material during insertion.

An embodiment of the present invention provides a catheter tip with a smoothly convex outer wall.

Other embodiments and advantages of the present invention shall become apparent to those skilled in the art upon a review of the following detailed description of the preferred embodiments and the accompanying drawings.

BRIEF DESCRIPTION OF THE DRAWINGS

FIG. 2 is a side view cutaway of the generally parabolic tip of the invention, illustrating the completely curved outer wall of the tip and the longitudinally circularly curved insertion end of the tip.

DETAILED DESCRIPTION OF THE PREFERRED EMBODIMENTS

Figure 1:
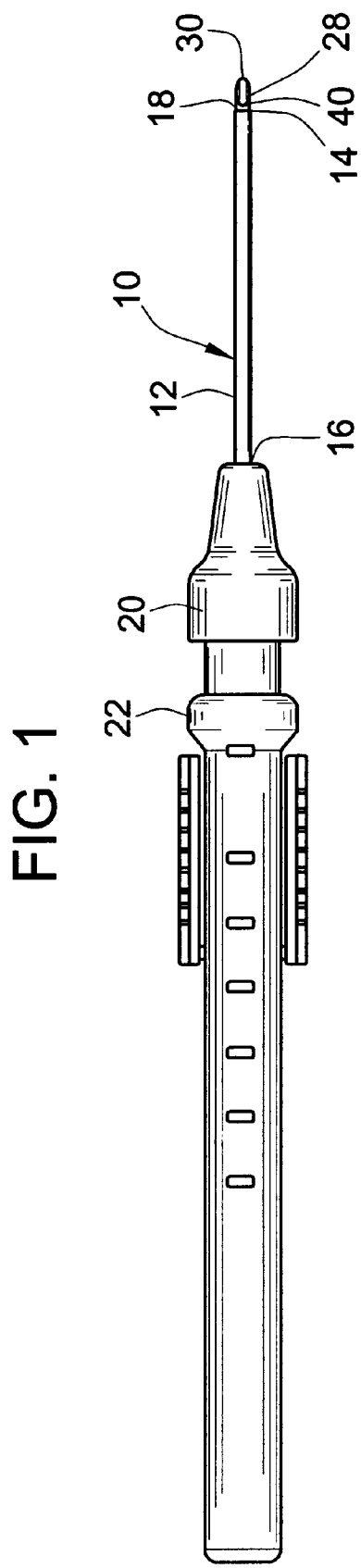
FIG. 1 is a plan view of the insertion device according to the present invention positioned on a handle assembly with a needle extending through the insertion device.

The preferred embodiment and best mode of the present invention will now be described in detail with reference being made to the drawings. The insertion device such as a catheter is indicated generally in the drawings by the reference number 10.

Referring to FIGS. 1 and 2, the catheter 10 includes a longitudinally extending tube 12 having a tip 14, located at the first end 18, and a second end 16. The second end 16 includes an attachment device 20 attaching the catheter 10 to, for example, a safety needle retraction assembly 22 or a luer-fitted coupling device (not shown). The tube 12 includes an interior surface 24 and an exterior surface 26. The interior surface 24 is adapted to receive a needle 28 having a pointed end 30.

The catheter 10 is typically comprised of a plastic material. In a preferred embodiment, the plastic material is polyurethane, but it can also be TEFLON or any commonly known catheter material. It has been found that polyurethane has a relatively low coefficient of drag or friction, but the invention contemplates that other suitable materials may also be used. A low coefficient of friction aids the insertion of the catheter 10 into the skin of a patient in a smooth and efficient manner. The catheter 10 and/or the needle 28 can be treated with a lubricant. In the preferred embodiment, the lubricant is a conventional silicone-based compound. The lubricant reduces friction between the catheter 10 and the skin of a patient during insertion.

Referring now to FIG. 2, in one preferred embodiment of a catheter having a tip formed according to the present invention, the tip 14 is substantially generally parabolic in profile having a length "L" 36, over which length the catheter tube 12 is smoothly and gradually reduced from its original wall thickness "t" 38 to intersect the surface of the needle 28 at catheter insertion end 40. The insertion end 40 is the end that is inserted, along with a needle 28, through a patient's skin. Over the length "L", the surface profile of the catheter tip 14 generally follows a smooth, substantially parabolic curve 32 except at the point of insertion into a patient's skin, 40. At this point, the surface profile of the insertion end becomes substantially circular, and is described by an arc on a circle having a radius "r", 42, as shown in FIG. 2. Length "L" may vary, and the generally parabolic surface profile 32 of tip 14 substantially flattens at or near point 34 where it assumes the generally cylindrical profile of the catheter tube with substantially parallel walls, with thickness "t" being relatively constant over the remaining length of tube 12 from point 34 to the second end 16 (as shown in FIG. 1). Thus, it will be seen that the substantially parabolic surface profile of tip 14 includes a narrowing of the profile to intersect the surface of needle 28 and includes a muting of the tip of the insertion end 40, which insertion end 40 assumes the shape of a an arc on a circle of radius "r" 42, at some point before the parabola intersects the surface of needle 28. The insertion end 40 then follows this circular profile until it intersects the needle surface 28, as illustrated in FIG. 2. It is this unique combination of the smoothly convex, generally parabolic narrowing-down of the catheter tube 14, terminating in a slight muting of the parabolic curve by means of the circular surface contour at the insertion end 40, that reduces the transition force while maintaining the physical integrity of the catheter material at the insertion end 40.

It should be noted that the parabolic profile is not configured such that its apex would intersect the circumference of the circle; if it did, it could create a dimple in the smoothly convex overall outer wall configuration. Rather, the apex of the parabola lies on the surface of the needle just beyond the point at which the circle of radius "r" intersects the surface of needle (28). Point "p" (46) defines a smooth, dimple-free transition between the parabolic and circular profiles of the tip 14 of the invention. Thus, the convex, parabolic shape is analogous to a comet tail, rolling over and out from the ball of the comet.

It is to be emphasized that the geometric characteristics described above are key in providing physical and operational integrity of the tip (i.e., prevent splitting and bunching and other side effects), and to minimize the transition force. The radius "r" is determined as an optimization between material strength and catheter penetration force. If "r" is too large the bulk profile of the tip makes penetration into the skin and vein high and not acceptable. If "r" is too small the material integrity is such that the tip can buckle going into the skin and vein and thus requires a high entry force. If "r" is too small the tip may also split or tear. Radius "r" is generally independent of catheter gauge.

We have found that "r" may vary between 0.0001 inch and 0.0030 inches, preferably between 0.0001 inch and 0.0020 inches, and most preferably between 0.0005 inches and 0.0010 inches, for most common catheter materials. It should be understood that other values for "r" may be readily achieved using different materials.

In addition, it is important that the tip 14 be of overall convex configuration and that a convex, smoothly curving shape be maintained from the tip over the entire length "L". Length "L" will vary depending upon the gauge of the catheter, and various lengths are considered within the scope of the invention.

By way of example and not by way of limitation, various dimensions for tips of the invention are provided in Table 1, wherein the radius and length are referenced in FIG. 2. Of course, different gauge catheters will have differently dimensioned tips, and the examples provided here are not intended to be exhaustive of all possible dimensions. For instance, for a very large catheter, "r" may be larger than the dimensions shown below. The lengths provided in table 1 are nominal lengths.

TABLE 1

| Sample | Gage | Radius, r (inch) | Length, L (inch) |
|---|---|---|---|
| 1 | 18 | 0.00040 | 0.075 |
| 2 | 18 | 0.00015 | 0.075 |
| 3 | 18 | 0.00010 | 0.075 |
| 4 | 18 | 0.00011 | 0.075 |
| 5 | 22 | 0.00010 | 0.063 |
| 6 | 22 | 0.00020 | 0.063 |

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

What is claimed is:

1. An insertion device comprising:
   a tube including a first end and a second end, the first and second ends defining a first passageway;
   a tip located at the first end, the tip including an inner wall and an outer wall and having an end with a circular cross-section which intersects the surface of a needle;
   wherein the outer wall contains no linear surfaces and the inner wall defines a substantially straight second passageway;
   wherein the tip has a parabolic profile in which the apex of the parabola lies on the surface of the needle just beyond the point at which the circular cross-section intersects the surface of the needle; and
   wherein the second end is adapted to receive an attachment device.

2. The insertion device of claim 1 wherein the second passageway is adapted to receive a piercing device.

3. The insertion device of claim 1, wherein the tip further comprises an insertion end including a point of insertion having a substantially arcuate profile, the arc being described by a circle having a radius (r), wherein the measurement of said radius is in the range of from about 0.0001 inches to about 0.0030 inches.

4. The insertion device of claim 1 wherein the tube is comprised of plastic.

5. The insertion device of claim 1, wherein the tube includes an interior surface and an exterior surface, said interior surface being adapted to receive a needle.

6. A catheter comprising:
   a tube including a first end and a second end having parallel walls and having a cylindrical profile;
   a tip having a profile, an insertion end; and a connecting surface;
   wherein the tip profile has a parabolic longitudinal configuration beginning at a point at which the cylindrical profile of the catheter tube first begins to narrow and the apex of the parabola lying on the surface of a needle; and
   wherein the insertion end has a point of insertion having a substantially circular profile adapted to intersect a surface of a needle.

7. The catheter of claim 6 wherein the tube is said catheter and wherein the second end includes attachment means for attaching the catheter to a device.

8. The catheter of claim 6, wherein the tube is comprised of plastic.

9. The catheter of claim 8, wherein said plastic is polyurethane.

10. The catheter of claim 6, wherein the tube includes an interior surface and an exterior surface, said interior surface being adapted to receive a needle.

11. An insertion device comprising:
   a tube including a tip having a profile, the tube further including a substantially cylindrical body;
   wherein the tip comprises an insertion end and a surface section connecting said insertion end with the substantially cylindrical body, and the tip having an end with a circular cross-section which intersects a surface of a needle;
   wherein the tip has a substantially curved surface profile; and
   wherein the insertion end and the connecting surface section together define a length (L).

* * * * *